United States Patent

Minai et al.

[11] Patent Number: 4,665,174
[45] Date of Patent: May 12, 1987

[54] PRODUCTION OF CYCLOPENTENONE DERIVATIVES

[75] Inventors: Masayoshi Minai, Moriyama; Tadashi Katsura, Hirakata, both of Japan

[73] Assignee: Sumitomo Chemical Company, Limited, Osaka, Japan

[21] Appl. No.: 377,050

[22] Filed: May 11, 1982

[30] Foreign Application Priority Data

May 12, 1981 [JP] Japan ................................. 56-71964
May 13, 1981 [JP] Japan ................................. 56-72448
Jun. 8, 1981 [JP] Japan ................................. 56-88706
Jun. 16, 1981 [JP] Japan ................................. 56-93312
Jul. 6, 1981 [JP] Japan ................................. 56-106122

[51] Int. Cl.$^4$ .................. C07D 279/10; C07D 265/30; C07C 85/02; C07C 87/50
[52] U.S. Cl. ..................................... 544/59; 558/253; 558/248; 564/446; 564/305; 568/42; 568/347; 548/556; 546/232; 546/301; 546/257; 546/339; 546/334; 546/223; 544/174; 549/66; 549/488; 549/75
[58] Field of Search .................... 260/455 R; 564/446, 564/305; 568/42, 347; 548/556; 546/232, 301, 257, 339; 544/174, 58.1, 59; 549/66, 488; 558/253, 248

[56] References Cited

U.S. PATENT DOCUMENTS 4,347,386 8/1982 Saito et al. ........................... 564/446
4,352,756 10/1982 Takisawa et al. ................... 564/446
4,356,326 10/1982 Saito et al. ........................... 564/446
4,398,043 8/1983 Saito et al. ........................... 564/446

OTHER PUBLICATIONS

Noller, Textbook of Organic Chemistry, W. B. Saunders Co., Philadelphia, 1966, p. 163.

Primary Examiner—Henry R. Jiles
Assistant Examiner—Robert C. Whittenbaugh
Attorney, Agent, or Firm—Birch, Stewart, Kolasch & Birch

[57] ABSTRACT

A process for preparing cyclopentenone derivatives of the formula:

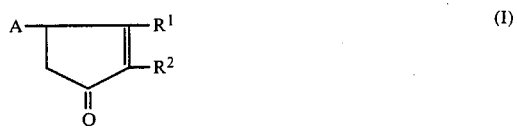

wherein $R^1$ is hydrogen, lower alkyl or lower alkenyl, $R^2$ is hydrogen, lower alkyl, lower alkenyl, lower alkynyl, cycloalkyl, substituted or unsubstituted aryl or substituted or unsubstituted ar(lower)alkyl and A is the residue of a nucleophilic agent from which a hydrogen atom is excluded, which comprises reacting a 3-hydroxy-4-cyclopentenone compound of the formula:

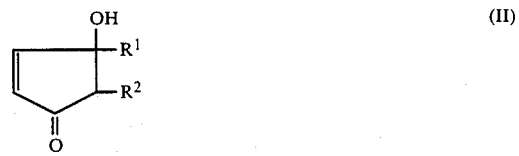

wherein $R^1$ and $R^2$ are each as defined above with a nucleophilic agent of the formula

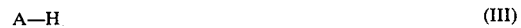

wherein A is as defined above.

The cyclopentenone derivatives of the formula (I) are useful as pharmaceuticals, agricultural chemicals, perfumes and as intermediates for the preparation of agricultural chemicals, pharmaceuticals and perfumes.

9 Claims, No Drawings

PRODUCTION OF CYCLOPENTENONE DERIVATIVES

The present invention relates to cyclopentenone derivatives and their production.

The said cyclopentenone derivatives are represented by the formula:

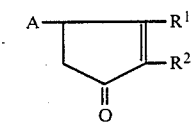
(I)

wherein $R^1$ is a hydrogen atom, a lower alkyl group or a lower alkenyl group, $R^2$ is a hydrogen atom, a lower alkyl group, a lower alkenyl group, a lower alkynyl group, a cycloalkyl group, a substituted or unsubstituted aryl group or a substituted or unsubstituted ar(-lower)alkyl group and A is the residue of a nucleophilic agent from which a hydrogen atom is excluded.

The residue of a nucleophilic agent from which a hydrogen atom is excluded may be, for instance, the residue of ammonia or an amine from which a hydrogen atom is eliminated, the residue of an alcohol from which a hydrogen atom is eliminated or the residue of hydrogen sulfide or a thiol from which a hydrogen atom is eliminated. Specifically, the substituent represented by the symbol A may be

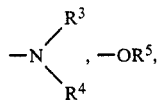

—$SR^6$ or the the like. $R^3$ can be, for instance, a hydrogen atom, a hydrocarbon group (e.g. lower alkyl, lower alkenyl, cycloalkyl, aryl, ar(lower)alkyl) optionally bearing any substituent(s), a lower alkoxy group, a hydroxyl group or a heterocyclic group optionally bearing any substituent(s). $R^4$ may be, for instance, a hydrogen atom or a hydrocarbon group (e.g. lower alkyl, lower alkenyl, aryl, ar(lower)alkyl) optionally bearing any substituent(s). Alternatively, $R^3$ and $R^4$ may be taken together with the nitrogen atom to which they are attached to form a heterocyclic group optionally bearing any substituent(s). $R^5$ is the residue of a hydroxyl-containing compound excluding hydroxyl therefrom and may be a hydrocarbon group (e.g. lower alkyl, lower alkenyl, lower alkadienyl, cycloalkyl, aryl, ar(-lower)alkyl) optionally bearing any substituent(s) or a heterocyclic group optionally bearing any substituent(s). $R^6$ is the residue of a mercapto-containing compound excluding mercapto therefrom and may be a hydrogen atom, a hydrocarbon group (e.g. lower alkyl, lower alkenyl, cycloalkyl, aryl, ar(lower)alkyl) optionally bearing any substituent(s), an acyl group or a heterocyclic group optionally bearing any substituent(s).

In the above significances, the term "lower" is intended to mean a group having not more than 12 carbon atoms, preferably not more than 8 carbon atoms. The term "cycloalkyl" is intended to mean the one having 3 to 8 carbon atoms. The term "aryl" means phenyl, naphthyl, etc. Examples of the heterocyclic group are pyrrolidino, piperidino, morpholino, thiomorpholino, pyridyl, thienyl, furyl, etc. The substituent(s) which may be present on the aryl group, the ar(lower)alkyl group, the hydrocarbon group or the heterocyclic group are halogen, lower alkyl, lower alkenyl, lower alkoxy, lower alkoxycarbonyl, lower alkanoyloxy, hydroxyl, hydroxy(lower)alkyl, phenyl, thienyl, furyl, pyridyl, etc. In case of the alkyl group, the preferred substituent(s) which may be present thereon are hydroxyl, lower alkoxy, lower alkanoyloxy, phenyl, thienyl, furyl, pyridyl, etc. The favorable substituent(s) which can be present on the aryl group are lower alkyl, lower alkoxy, halogen, etc. The favored examples of the substituent(s) which can be present on the heterocyclic group are hydroxyl, hydroxy(lower)alkyl, lower alkoxycarbonyl, etc. The term "acyl" is intended to mean lower alkanoyl, optionally substituted benzoyl, optionally substituted phenylalkanoyl, alkoxycarbonyl, etc. Therefore, examples of the ar(lower)alkyl group optionally bearing any substituent(s) may include benzyl, α-methylbenzyl, phenethyl, naphthylmethyl, 4-methylphenylmethyl, 4-methoxyphenylmethyl, 4-chlorophenylmethyl, 2,4-dichlorophenylmethyl, etc.

Some analogous compounds to the cyclopentenone derivatives (I) and their production are known and can be summarized as follows:

Tetrahedron, Vol. 36, 661 (1980)  (1)

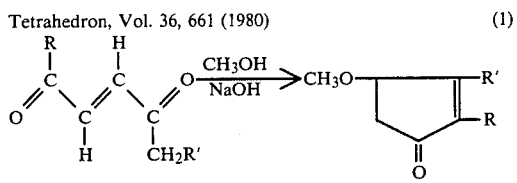

wherein R is hydrogen or methyl and R' is $C_7H_{15}$ or $C_{11}H_{23}$.

J. Chem. Soc., 239 (1944)  (2)

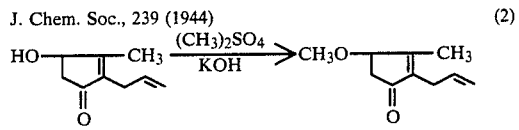

J. Org. Chem., Vol. 45, 4500 (1980)  (3)

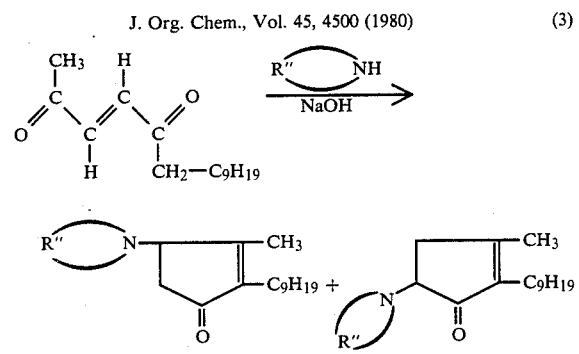

wherein R'' is —$(CH_2)_4$—, —$(CH_2)_5$—, —$(CH_2)_2$—O—$(CH_2)_2$—.

In these procedures, however, the yields of the products are poor. Further, the references (1) and (2) disclose 4-methoxy compounds only and are entirely silent on other compounds having any group other than methoxy at the 4-position. The procedure in the reference (3) is disadvantageous for the production of 4-substituted compounds, because 5-substituted compounds are by-produced in addition to the 4-substituted compounds. Particularly when alkylamines such as diethylamine are used as the reagent, there are obtained a mixture of various products, and in fact, their isolation and identification have not been made. Furthermore, none of the said references discloses any use of the products therein.

The cyclopentenone derivatives (I) are useful as pharmaceuticals, agricultural chemicals, perfumes, etc. and their intermediates. For instance, the cyclopentenone derivatives (I) are reacted with chrysanthemic acid, 2,2,3,3-tetramethylcyclopropane carboxylic acid, p-chlorophenylisovaleric acid, etc. to give their esters or amides, which are useful as agricultural chemicals. Further, for instance, the cyclopentenone derivatives (I) may be reacted with α-substituted phenyl acetic acids to give their esters or amides, which are useful as anti-inflammatory agents. Furthermore, for instance, they can be used as intermediates for the synthesis of novel derivatives of prostaglandins. Moreover, they are advantageous for pharmaceutical use, because they are more lipophilic than their known analogous compounds. Moreover, those wherein $R^5$ is geranyl are useful as perfumes having good odor or their intermediates.

The cyclopentenone derivatives of the formula (I) can be readily produced in excellent yields by reacting a 3-hydroxy-4-cyclopentenone compound of the formula:

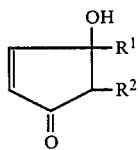
(II)

wherein $R^1$ and $R^2$ are each as defined above with a nucleophilic agent of the formula:

A—H  (III)

wherein A is as defined above. This reaction is per se novel.

The starting 3-hydroxy-4-cyclopentenone compound (II) is known and can be produced, for instance, from the corresponding furan-carbinol by rearrangement as shown in the following formulas:

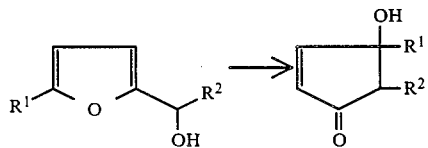

wherein $R^1$ and $R^2$ are each as defined above.

Examples of the 3-hydroxy-4-cyclopentenone compound (II) are as follows: 2-methyl-3-hydroxy-4-cyclopentenone, 2-ethyl-3-hydroxy-4-cyclopentenone, 2-n-propyl-3-hydroxy-4-cyclopentenone, 2-isopropyl-3-hydroxy-4-cyclopentenone, 2-n-butyl-3-hydroxy-4-cyclopentenone, 2-n-pentyl-3-hydroxy-4-cyclopentenone, 2-n-hexyl-3-hydroxy-4-cyclopentenone, 2-n-heptyl-3-hydroxy-4-cyclopentenone, 2-allyl-3-hydroxy-4-cyclopentenone, 2-(2'-cis-butenyl)-3-hydroxy-4-cyclopentenone, 2-(2'-cis-pentenyl)-3-hydroxy-4-cyclopentenone, 2-(3'-cis-hexenyl)-3-hydroxy-4-cyclopentenone, 2-(2'-trans-pentenyl)-3-hydroxy-4-cyclopentenone, 2-propargyl-3-hydroxy-4-cyclopentenone, 2-(2'-pentynyl)-3-hydroxy-4-cyclopentenone, 2-benzyl-3-hydroxy-4-cyclopentenone, 2-p-chlorobenzyl-3-hydroxy-4-cyclopentenone, 2-p-methoxybenzyl-3-hydroxy-4-cyclopentenone, 2-phenyl-3-hydroxy-4-cyclopentenone, 2-cyclopentyl-3-hydroxy-4-cyclopentenone, 2-cyclohexyl-3-hydroxy-4-cyclopentenone, 2-(α-methylallyl)-3-hydroxy-4-cyclopentenone, 2-(3',4'-methylenedioxyphenyl)-3-hydroxy-4-cyclopentenone, 2-allyl-3-hydroxy-3-methyl-4-cyclopentenone, 2-(2'-cis-pentenyl)-3-hydroxy-3-methyl-4-cyclopentenone, 2-n-pentyl-3-hydroxy-3-methyl-4-cyclopentenone, 2-(2'-cis-butenyl)-3-hydroxy-3-methyl-4-cyclopentenone, 2-n-hexyl-3-hydroxy-3-methyl-4-cyclopentenone, 2-(3'-cis-hexenyl)-3-hydroxy-3-methyl-4-cyclopentenone, 2-cyclopentyl-3-hydroxy-3-methyl-4-cyclopentenone, 2-cyclohexyl-3-hydroxy-3-methyl-4-cyclopentenone, 2-phenyl-3-hydroxy-3-methyl-4-cyclopentenone, 2-p-chlorophenyl-3-hydroxy-4-cyclopentenone, 2-p-methoxyphenyl-3-hydroxy-3-methyl-4-cyclopentenone, 2-benzyl-3-hydroxy-3-methyl-4-cyclopentenone, 2-(3',4'-dimethoxybenzyl)-3-hydroxy-3-methyl-4-cyclopentenone, 2-n-pentyl-3-allyl-3-hydroxy-4-cyclopentenone, etc.

Examples of the nucleophilic agent (III) include amines, hydroxyl-containing compounds, sulfur compounds, etc. Specific examples of the amines are ammonia, hydroxylamine, o-methylhydroxylamine, N-methylhydroxylamine, methylamine, ethylamine, n- or iso-propylamine, n- or sec-butylamine, n-, iso- or tert-pentylamine, n-, sec- or tert-octylamine, cyclopropylamine, octadecylamine, aminoadamantane, allylamine, dimethylamine, diethylamine, di-n-propylamine, cyclohexylamine, cyclopentylamine, aminoethanol, aminobutanol, 3-amino-1-propanol, 1-amino-2-propanol, L-2-amino-1-propanol, N-aminopiperidine, ω-amino-β-picoline, 4(6)-aminouracil, 3-aminopropionitrile, 2-aminopyridine, 2-aminomethylpyridine, aminomethylthiophene, furfurylamine, aniline, 4-chloroaniline, 2,4-dichloroaniline, 4-methylaniline, 3- or 4-hydroxyaniline, 4-methoxyaniline, N-methylaniline, o-, m- or p-nitroaniline, 4-hydroxyaniline, 3,4-methylenedioxyaniline, 3,4-dimethoxyaniline, benzylamine, β-phenethylamine, α-methylbenzylamine, d-α-methylbenzylamine, ethylenediamine, 2,2-dimethyl-3-(2-methyl-1-propenyl)cyclopropyl-1-methylamine, 1-2-hydroxymethylpyrrolidine, 1-2-methoxycarbonylpyrrolidine, 1-2-methoxycarbonyl-4-hydroxypyrrolidine, etc. As the organic hydroxyl-containing compounds, there may be exemplified alcohols (e.g. isopropanol, n-propanol, n-butanol, n-octanol, dodecanol, ethylene glycol, 1,3-propanediol, allyl alcohol, 2-pentenyl alcohol, 3-hexenyl alcohol, geraniol, nerol, farnesyl alcohol, cyclopentanol, cyclohexanol, 2-cyclohexenyl alcohol, cyclopropyl methyl alcohol, l-menthol, propargyl alcohol, 2-pentyn-1-ol, 1,4-cyclohexanediol, dimethylaminoethanol, dimethylaminopropanol, diethylaminoethanol, furfuryl alcohol, thenyl alcohol, 2,2-dimethyl-3-(2-methyl-1-propenyl)cyclopropyl-1-methanol), phenols (e.g. phenol, cresol, 4-chlorophenol, 2,4-dichlorophenol, 4-dimethylaminophenol, 4-sulfamoylphenol, catechol, resorcinol, hydroquinone, sesamol, 4-methoxyphenol), aralkyl alcohols (e.g. benzyl alcohol, l-α-methylbenzyl alcohol, d-α-methyl-benzyl alcohol, 3,4-methylenedioxybenzyl alcohol, 2,4-dichlorobenzyl alcohol, 3,4-dimethoxybenzyl alcohol, β-phenethyl alcohol), diisopropylidene mannose, diisopropylidene glucose, glycolic acid ethyl ester, mandelic acid methyl ester, pantoyl lactone, etc. As the sulfur compounds, there may be exemplified alkyl, alkenyl or cycloalkyl mercaptans (e.g. methylmercaptan, ethylmercaptan, n- or iso-propylmercaptan, n- or iso-butylmercaptan, mercaptodecane, mercaptononane, mercaptocyclopentane, mercaptocyclohexane, 3-mercapto-1-propene), aryl or aralkylmercaptans (e.g. thiophenol, o-, m- or p-mercaptotoluene, p-chlorothiophenol, ω-mercaptotoluene, β-mercaptonaphthalene), carboxy- or hydroxy-substituted alkyl or aryl mercaptans (e.g. mercaptoacetic acid, 2- or 3-mercaptopropionic acid, o-mercaptobenzoic acid, p-hydroxymercaptobenzene, 2-hydroxyethylmercaptan, 3-mercapto-1,2-propanediol), thiocarboxylic acids (e.g. thioacetic acid, thiopropionic acid), heterocyclic ring-containing mercaptans (e.g. mercaptobenzothiazole, 2- or 4-mercaptopyridine, 2-mercapto-5-thiazolidone, 2-mercaptothiazoline, 2-mercaptobenzoxazole, 2-mercaptothiophene), etc.

The reaction between the 3-hydroxy-4-cyclopentenone compound (II) and the nucleophilic agent (III) is carried out in the presence or absence of an inert solvent, when desired, in the presence of a catalyst.

As the inert solvent, there may be used water, ethers (e.g. dioxane, tetrahydrofuran, diethyl ether, di-n-propyl ether), ketones (e.g. acetone, methylethylketone), esters (e.g. methyl acetate, ethyl acetate), dimethylformamide, dimethylsulfoxide, hydrocarbons (e.g. benzene, toluene), halogenated hydrocarbons (e.g. chloroform, dichloromethane), etc. Their mixtures are also usable. Further, excess of the nucleophilic agent (III) may be used as the reaction medium.

When the nucleophilic agent (III) is a hydroxyl-containing compound or a sulfur compound, it is preferred to effect the reaction under anhydrous conditions for achievement of a higher reaction rate or a better yield. Thus, the operation in such an organic solvent as tetrahydrofuran, chloroform, dioxane or toluene in the presence of a catalyst is recommended. When the nucleophilic agent (III) is an amine, anhydrous conditions are not necessarily recommended, and particularly when the amine is water-soluble, an aqueous solution of such amine is frequently and favorably used. In this case, the combined use of any organic solvent with water is also permissible. In case of the amine being not water-soluble, however, the operation in an organic solvent, especially under anhydrous conditions, is usually preferred.

As the catalyst, there may be used any one chosen from alkali metals (e.g. sodium, potassium, lithium) and their salts (e.g. nitrate, sulfate, chloride, phosphate), oxides, alkoxides, hydrides and amides, tertiary amines (e.g. pyridine, triethylamine, quinine), quaternary ammonium salts, etc. When the nucleophilic agent (III) is an amine, such amine itself plays a role of the catalyst. Even in such case, any other compound which serves as the catalyst may be added to the reaction medium. The use of the catalyst is normally effective for enhancement of the reaction rate and increase of the conversion. While any particular limitation is not present on the amount of the catalyst, it is usual to employ the catalyst in an amount of 1/1000 to 2 parts by weight, preferably of 1/500 to 1/2 part by weight, to 1 part by weight of the 3-hydroxy-4-cyclopentenone compound (II).

The reaction temperature is usually from −20° to 150° C., preferably from −10° to 120° C. Any special limitation is not present on the reaction time.

As the result of the above reaction, there is readily produced the objective cyclopentenone derivative (I) in an excellent yield. Recovery of the cyclopentenone derivative (I) from the reaction mixture may be attained by a per se conventional separation procedure such as extraction, fractionation, condensation, distillation or recrystallization.

Practical and presently preferred embodiments of the invention are illustratively shown in the following Examples wherein part(s) and % are by weight unless otherwise indicated.

EXAMPLE 1

Into a four-necked flask equipped with a stirrer and a thermometer, a 30% aqueous solution of monoethylamine (70 g) and tetrahydrofuran (18 g) were charged, and then 2-n-pentyl-3-hydroxy-3-methyl-4-cyclopentenone (18.2 g) was dropwise added thereto at a temperature of 10° to 20° C. for 30 minutes. At the same temperature, the reaction mixture was kept for 2 hours. After completion of the reaction, the mixture was extracted with toluene, and the organic layer was washed with water. From the organic layer, toluene was evaporated off to give 2-n-pentyl-3-methyl-4-ethylamino-2-cyclopentenone (20.3 g). Yeild, 97%. The product was purified by alumina chromatography using toluene-ethyl acetate (10:1 by volume). $n_D^{20}$ 1.4864.

EXAMPLE 2

2-Allyl-3-hydroxy-3-methyl-4-cyclopentenone (15.2 g) was dropwise added to a 40% aqueous solution of dimethylamine (60 g) in the same flask as used in Example 1 at a temperature of 10° to 20° C. for 30 minutes. At the same temperature, the reaction mixture was kept for 1 hour. After completion of the reaction, the mixture was treated and purified in the same manner as in Example 1 to obtain 2-allyl-3-methyl-4-dimethylamino-2-cyclopentenone (17.3 g). Yield, 96.5%. $n_D^{20}$ 1.4997.

EXAMPLE 3

2-Ethyl-3-hydroxy-4-cyclopentenone (12.6 g) was dropwise added to a mixture of allylamine (25 g) and toluene (25 g) in the same flask as used in Example 1 at a temperature of 10° to 20° C. for 1 hour. The reaction mixture was kept at a temperature of 20° to 30° C. for 3 hours. After completion of the reaction, the mixture was treated and purified in the same manner as in Example 1 to obtain 2-ethyl-4-allylamino-2-cyclopentenone (15.7 g). Yield, 95%. $n_D^{20}$ 1.4924.

EXAMPLE 4

Into the same flask as used in Example 1, 2-allyl-3-hydroxy-3-methyl-4-cyclopentenone (15.2 g), aniline (30 g), triethylamine (0.8 g) and toluene (45 g) were charged, and the mixture was stirred under a nitrogen stream at a temperature of 40° to 70° C. for 2 hours. After completion of the reaction, the mixture was treated and purified in the same manner as in Example 1 to obtain 2-allyl-3-methyl-4-anilino-2-cyclopentenone (22 g). Yield, 97%. $n_D^{20}$ 1.5880.

EXAMPLE 5

2-Allyl-3-hydroxy-3-methyl-4-cyclopentenone (15.2 g) was dropwise added to a 40% aqueous solution of monomethylamine (60 g) in the same flask as used in Example 1 at a temperature of 10° to 20° C. for 1 hour. At the same temperature, the reaction mixture was kept for 1 hour. After completion of the reaction, monomethylamine and water were evaporated off under reduced pressure. The residue was extracted with dichloromethane, and the solvent was evaporated off from the organic layer to obtain 2-allyl-3-methyl-4-methylamino-2-cyclopentenone (15.9 g). Yield, 96%. $n_D^{23}$ 1.5090.

EXAMPLE 6

2-Allyl-3-hydroxy-3-methyl-4-cyclopentenone (15.2 g) was dropwise added to a 25% aqueous solution of N-methylhydroxylamine (30 g) in the same flask as used in Example 1 at a temperature of 15° to 25° C. for 1 hour. At the same temperature, the reaction mixture was kept for 2 hours. After completion of the reaction, the mixture was treated and purified in the same manner as in Example 5 to obtain 2-allyl-3-methyl-4-(N-hydroxy-N-methylamino)-2-cyclopentenone (16.5 g). Yield, 91%. $n_D^{20}$ 1.5102.

EXAMPLES 7 TO 23

In the same manner as above, there were prepared cyclopentenone derivatives (I) as shown in Table 1, wherein the amount of the 3-hydroxy-4-cyclopentenone compound (II) used was one part.

TABLE 1

| Example No. | Starting materials 3-Hydroxy-4-cyclopentenone compound (II) R¹ | R² | Nucleophilic agent (III) (part) | Catalyst (part) | Solvent (part) | Reaction condition Temperature (°C.) | Time (hr) | Cyclopentenone derivative (I)[*1] $\diagdown N \diagup^{R^3}_{R^4}$ | Physical property | Yield (%) |
|---|---|---|---|---|---|---|---|---|---|---|
| 7 | —CH₃ | —CH₂CH=CH₂ | 28% Aqueous ammonia (4) | — | — | 10–20 | 1 | —NH₂ | $n_D^{20}$ 1.5114 | 95 |
| 8 | —CH₃ | —C₅H₁₁(n) | 28% Aqueous ammonia (4) | — | Tetrahydrofuran (1) | 10–20 | 1 | —NH₂ | $n_D^{20}$ 1.4992 | 94 |
| 9 | —CH₃ | —CH₂CH=CH₂ | d-α-Methylbenzylamine (2) | Triethylamine (1/20) | Toluene (3) | 30–70 | 3 | —NH—CH(CH₃)(C₆H₅) | $n_D^{17}$ 1.5478 | 96 |
| 10 | —CH₃ | —CH₂CH=CH₂ | 40% Aqueous aminoethanol (2) | — | — | 10–20 | 3 | —NHCH₂CH₂OH | $n_D^{20}$ 1.5183 | 92 |
| 11 | —CH₃ | —CH₂CH=CH₂ | 2-Amino-1-butanol (1.5) | Pyridine (1/20) | Tetrahydrofuran (2) | 20–50 | 1 | —NH—CH(C₂H₅)CH₂OH | $n_D^{20}$ 1.5126 | 95 |
| 12 | —CH₃ | —CH₂CH=CH₂ | 1-2-Amino-1-propanol (1.5) | — | Water (3) | 30–50 | 1 | —NH—CH(CH₃)CH₂OH | $n_D^{20}$ 1.5177 | 94.5 |
| 13 | —CH₃ | —CH₂CH=CH₂ | N—Aminopiperidine (2) | — | Chloroform (3) | 30–60 | 3 | —NH—N(piperidine) | $n_D^{20}$ 1.5258 | 98 |
| 14 | —CH₃ | —CH₂CH=CH₂ | Cyclopropylmethylamine (2) | — | Water (4) | 15–30 | 2 | —NH—CH₂(cyclopropyl) | $n_D^{18}$ 1.5110 | 97 |
| 15 | —CH₃ | —CH₂CH=CH₂ | 2-Aminomethylpyridine (2) | — | Toluene (2) | 30–60 | 3 | —NH—CH₂(2-pyridyl) | $n_D^{18}$ 1.5786 | 93.5 |
| 16 | —H | —C₅H₁₁(n) | 40% Aqueous monomethylamine (3) | — | Tetrahydrofuran (1) | 20–25 | 2 | —NHCH₃ | $n_D^{20}$ 1.5011 | 96 |

TABLE 1-continued

| Example No. | Starting materials 3-Hydroxy-4-cyclopentenone compound (II) R¹ | R² | Nucleophilic agent (III) (part) | Catalyst (part) | Solvent (part) | Reaction condition Temperature (°C.) | Time (hr) | Cyclopentenone derivative (I)[*1] -N(R³)(R⁴) | Physical property | Yield (%) |
|---|---|---|---|---|---|---|---|---|---|---|
| 17 | —CH₃ | —CH₂CH=CHCH₂CH₃ | 4-Chloro-aniline (2) | Triethyl-amine (1/20) | Toluene (2) | 40–70 | 4 | —NH—C₆H₄Cl (4-Cl) | $n_D^{20}$ 1.5902 | 94 |
| 18 | —H | —CH₂—C₆H₅ | 30% Aqueous monoethyl-amine (3) | — | Tetrahydro-furan (3) | 20–35 | 2 | —NHC₂H₅ | $n_D^{20}$ 1.5530 | 92 |
| 19 | —CH₃ | —CH₂—C₆H₁₁ (cyclohexyl) | n-Pentyl-amine (2) | Pyridine (1/30) | Toluene (2) | 30–60 | 3 | —NHC₅H₁₁ | $n_D^{20}$ 1.4986 | 93 |
| 20 | —CH₃ | —CH₂C≡CCH₂CH₃ | β-Phenethyl-amine (2) | Triethyl-ethyl (1/20) | Toluene (2) | 30–70 | 5 | —NHCH₂CH₂—C₆H₅ | $n_D^{20}$ 1.5436 | 91 |
| 21 | —CH₃ | —CH₂—C₆H₅ | 40% Aqueous monomethyl-amine (3) | — | Tetrahydro-furan (2) | 20–30 | 5 | —NHCH₃ | $n_D^{20}$ 1.5512 | 96 |
| 22 | —CH₃ | —CH₂CH=CH₂ | O—Methyl-hydroxyl-amine (1) | — | Water (3) | 10–25 | 2 | —NHOCH₃ | $n_D^{20}$ 1.5046 | 91 |
| 23 | —CH₃ | —CH₂CH=CH₂ | 2-Amino-methylthio-phene (2) | Pyridine (1/30) | Toluene (2) | 30–70 | 4 | —NHCH₂—(2-thienyl) | $n_D^{20}$ 1.5614 | 92 |

Note:
R¹ and R² in the cyclopentenone derivatives (I) have the same meanings as in the 3-hydroxy-4-cyclopentenone compound (II).

EXAMPLE 24

Into the same flask as used in Example 1, 2-allyl-3-hydroxy-3-methyl-4-cyclopentenone (15.2 g), L-prolinol (18 g), toluene (100 g) and a solution of n-butyl lithium (0.3 g) in hexane (3 ml) were charged, and the mixture was stirred under a nitrogen stream at a temperature of 25° to 45° C. for 5 hours. After completion of the reaction, the mixture was treated and purified in the same manner as in Example 1 to obtain 2-allyl-3-methyl-4-l-(2'-hydroxymethylpyrrolidino)-2-cyclopentenone (22.3 g). Yield, 95% $N_D^{20}$ 1.5288.

EXAMPLE 25

Into the same flask as used in Example 1, 2-allyl-3-hydroxy-3-methyl-4-cyclopentenone (0.1 mol; 1 part), 2-cis-pentenol (5 parts) and sodium hydride (1/30 part) were charged, and the mixture was stirred at a temperature of 10° to 15° C. for 1 hour. After completion of the reaction, the mixture was neutralized with 1N HCl and extracted with toluene. Toluene was evaporated off from the organic layer to obtain 2-allyl-3-methyl-4-(2-cis-pentenyloxy)-2-cyclopentenone, which was purified by chromatography. Yield, 97%. $n_D^{20}$ 1.4946.

EXAMPLE 26

Into the same flask as used in Example 1, 2-n-pentyl-3-hydroxy-3-methyl-4-cyclopentenone (0.1 mol; 1 part), n-propanol (5 parts) and p-toluenesulfonic acid (1/20 part) were charged, and the mixture was stirred at a temperature of 40° to 70° C. for 5 hours. After completion of the reaction, the mixture was treated in the same manner as in Example 25 to obtain 2-n-pentyl-3-methyl-4-n-propoxy-2-cyclopentenone. Yield, 96%. $n_D^{19}$ 1.4792.

EXAMPLE 27

2-Allyl-3-hydroxy-3-methyl-4-cyclopentenone (0.1 mol; 1 part) was dropwise added to a mixture of 3,4-dimethoxybenzyl alcohol (4 parts), tetrahydrofuran (4 parts) and sodium hydride (1/40 part) in the same flask as used in Example 1 at a temperature of 10° to 20° C. for 30 minutes. Then, the reaction mixture was stirred at the same temperature for 1 hour. After completion of the reaction, the mixture was treated in the same manner as in Example 25 to obtain 2-allyl-3-methyl-4-(3,4-dimethoxybenzyloxy)-2-cyclopentenone. Yield, 96%. $n_D^{20}$ 1.5514.

EXAMPLE 28

Into the same flask as used in Example 1, 2-allyl-3-hydroxy-3-methyl-4-cyclopentenone (0.1 mol; 1 part), phenol (6 parts) and triethylamine (1/5 part) were charged and stirred at a temperature of 50° to 80° C. for 4 hours. The reaction mixture was treated in the same manner as in Example 25 to obtain 2-allyl-3-methyl-4-phenoxy-2-cyclopentenone. Yield, 95%. $n_D^{20}$ 1.5539.

EXAMPLE 29

Into the same flask as used in Example 1, 2-allyl-3-hydroxy-3-methyl-4-cyclopentenone (0.1 mol; 1 part), resorcinol (5 parts), tetrahydrofuran (½ part) and triethylamine (1/10 part) were charged, and the mixture was stirred at a temperature of 50° to 80° C. for 2 hours. After completion of the reaction, toluene (6 parts) and water (2 parts) were added thereto, and the separated organic layer was washed with a 5% aqueous solution of sodium carbonate. Toluene was evaporated off from the organic layer to give 2-allyl-3-methyl-4-(3-hydroxyphenoxy)-2-cyclopentenone. Yield, 95%. The product was purified by recrystallization from a mixture of chloroform and methanol (5:2 by volume). $n_D^{20}$ 1.5707.

EXAMPLES 30 to 49

In the same manner as above, there were prepared the cyclopentenone derivatives (I) as shown in Table 2, wherein the amount of the 3-hydroxy-4-cyclopentenone compound (II) used was one part.

TABLE 2

| Example No. | Starting materials 3-Hydroxy-4-cyclopentenone compound (II) R¹ | R² | Nucleophilic agent (III) (part) | Catalyst (part) | Solvent (part) | Reaction condition Temperature (°C.) | Time (hr) | Cyclopentenone derivative (I)*¹ —OR⁵ | Physical property | Yield (%) |
|---|---|---|---|---|---|---|---|---|---|---|
| 30 | —CH₃ | n-Hexyl | Methoxy-ethanol (5) | Sodium ethoxide (1/30) | Toluene (1) | 20–40 | 1 | —O—CH₂CH₂OCH₃ | $n_D^{15}$ 1.4862 | 98 |
| 31 | —CH₃ | Allyl | 2,2-Dimethyl-3-isobutenyl-cyclopropyl-methyl alcohol (5) | Sodium hydride (1/20) | Tetrahydro-furan (1/2) | 10–20 | 1 | 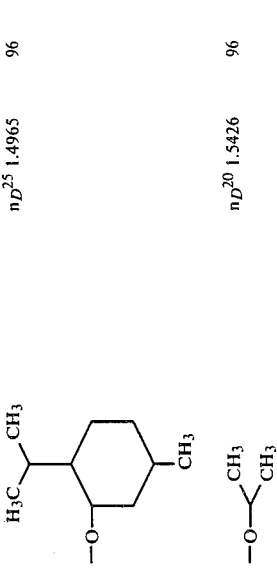 | $n_D^{20}$ 1.5016 | 97 |
| 32 | —CH₃ | Allyl | l-Menthol (4) | Sodium hydride (1/20) | Tetrahydro-furan (1/2) | 10–20 | 2 | 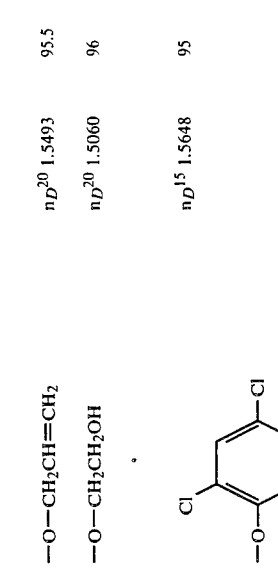 | $n_D^{25}$ 1.4965 | 96 |
| 33 | —H | Benzyl | Isopropanol (6) | Tetrabutyl-ammonium bromide (1/40) Triethyl-amine (1/50) | — | 40–70 | 3 | 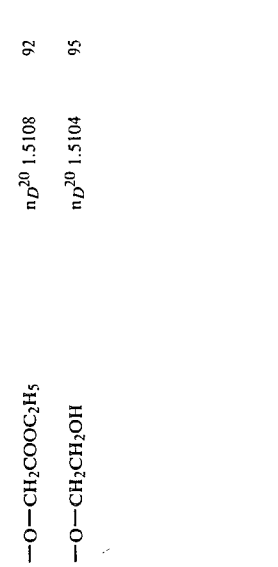 | $n_D^{20}$ 1.5426 | 96 |
| 34 | —CH₃ | Phenyl | Allyl alcohol (5) | Sodium hydride (1/30) | — | 20–30 | 2 | —O—CH₂CH=CH₂ | $n_D^{20}$ 1.5493 | 95.5 |
| 35 | —CH₃ | Allyl | Ethylene glycol (7) | Sodium methoxide (1/50) | — | 20–40 | 1 | —O—CH₂CH₂OH | $n_D^{20}$ 1.5060 | 96 |
| 36 | —CH₃ | Allyl | 2,4-Dichloro-phenol (6) | Triethyl-amine (1/10) | Tetrahydro-furan (1) | 50–80 | 4 |  | $n_D^{15}$ 1.5648 | 95 |
| 37 | —CH₃ | Allyl | Glycollic acid ethyl ester (5) | n-Butyl lithium (1/20) | Tetrahydro-furan (1) | 20–50 | 4 | —O—CH₂COOC₂H₅ | $n_D^{20}$ 1.5108 | 92 |
| 38 | —CH₃ | 2-cis-Pentenyl | Ethylene glycol (6) | Sodium hydride (1/3) | — | 10–20 | 2 | —O—CH₂CH₂OH | $n_D^{20}$ 1.5104 | 95 |

TABLE 2-continued

| Example No. | Starting materials 3-Hydroxy-4-cyclopentenone compound (II) R¹ | R² | Nucleophilic agent (III) (part) | Reaction condition Solvent (part) | Catalyst (part) | Temperature (°C.) | Time (hr) | Cyclopentenone derivative (I)*1 —OR⁵ | Physical property | Yield (%) |
|---|---|---|---|---|---|---|---|---|---|---|
| 39 | —CH₃ | Allyl | Cathecol (5) | Tetrahydrofuran (1) | Triethylamine (1/10) | 50-80 | 2 | —O—(2-hydroxyphenyl) | $n_D^{20}$ 1.5710 | 96 |
| 40 | —CH₃ | Allyl | Hydroquinone (6) | Tetrahydrofuran (1) | Pyridine (1/10) | 50-80 | 2 | —O—(4-hydroxyphenyl) | $n_D^{20}$ 1.5716 | 97 |
| 41 | —CH₃ | Allyl | Geraniol (5) | — | Sodium hydride (1/40) | 10-20 | 1 | —O-geranyl | $n_D^{20}$ 1.5032 | 96 |
| 42 | —CH₃ | n-Pentyl | Geraniol (5) | — | Sodium hydride (1/30) | 10-20 | 1 | —O-geranyl | $n_D^{15}$ 1.4986 | 95.5 |
| 43 | —CH₃ | Allyl | d-α-Methylbenzyl alcohol (4) | Tetrahydrofuran (1) | Sodium hydride (1/30) | 10-20 | 1 | —O—CH(CH₃)—phenyl | $n_D^{20}$ 1.5332 | 96 |
| 44 | —CH₃ | Allyl | Sesamol (5) | Tetrahydrofuran (1) | Triethylamine (1/20) | 50-80 | 4 | —O-(benzo[1,3]dioxol-yl) | $n_D^{20}$ 1.5613 | 90 |
| 45 | —CH₃ | Cyclohexyl | Furfuryl alcohol (5) | — | Sodium hydride (1/30) | 10-20 | 2 | —O—CH₂-(2-furyl) | $n_D^{20}$ 1.4886 | 96 |
| 46 | —CH₃ | Allyl | N,N—Dimethylaminoethyl alcohol (5) | — | Sodium hydride (1/30) | 10-20 | 2 | —O—CH₂CH₂N(CH₃)₂ | $n_D^{20}$ 1.5011 | 95 |

TABLE 2-continued

| Example No. | Starting materials 3-Hydroxy-4-cyclo-pentenone compound (II) R¹ | R² | Nucleophilic agent (III) (part) | Catalyst (part) | Solvent (part) | Reaction condition Temperature (°C.) | Time (hr) | Cyclopentenone derivative (I)*1 —OR⁵ | Physical property | Yield (%) |
|---|---|---|---|---|---|---|---|---|---|---|
| 47 | —CH₃ | Allyl | Pentoyl lactone (3) | n-Butyl lithium (1/10) | Tetrahydrofuran (2) | 20–30 | 4 | 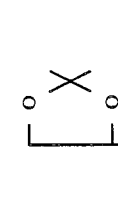 | $n_D^{20}$ 1.5115 | 90 |
| 48 | —CH₃ | Allyl | Diisopropylidene mannose (3) | n-Butyl lithium (1/20) | Tetrahydrofuran (2) | 10–30 | 5 | 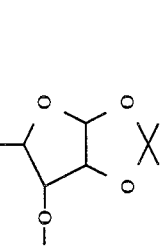 | $n_D^{20}$ 1.4915 | 91 |
| 49 | —CH₃ | Allyl | Diisopropylidene glucose (4) | n-Butyl lithium (1/10) | Tetrahydrofuran (2) | 15–35 | 3 |  | $n_D^{20}$ 1.4883 | 92 |

Note:
R¹ and R² in the cyclopentenone derivatives (I) have the same meanings as in the 3-hydroxy-4-cyclopentenone compound (II).

EXAMPLE 50

Into the same flask as used in Example 1, 2-allyl-3-hydroxy-3-methyl-4-cyclopentenone (15.2 g), isopropylmercaptan (20 g), triethylamine (1 g) and toluene (45 g) were charged, and the mixture was stirred under a nitrogen stream at a temperature of 40° to 70° C. for 5 hours. After completion of the reaction, the mixture was washed with an acid, an alkali and water in order. The organic layer was separated and concentrated to give 2-allyl-3-methyl-4-isopropylthio-2-cyclopentenone (20.2 g). Yield, 96.3%. The product was purified by silica gel chromatography using toluene-ethyl acetate (10:1 by volume). $n_D^{20}$ 1.5196.

EXAMPLE 51

Into the same flask as used in Example 1, thioacetic acid (35 g) and triethylamine (7 g) were charged, and 2-n-pentyl-3-hydroxy-3-methyl-4-cyclopentenone (18.2 g) was dropwise added thereto at a temperature of 20° to 35° C. for 1 hour. Thereafter, the reaction mixture was stirred at a temperature of 40° to 60° C. for 3 hours. After completion of the reaction, the mixture was diluted with toluene (50 ml) and treated in the same manner as in Example 50 to obtain 2-n-pentyl-3-methyl-4-acetylthio-2-cyclopentenone (24.1 g). Yield, 94%. $n_D^{20}$ 1.5146.

EXAMPLE 52

Into the same flask as used in Example 1, thiophenol (10 g), triethylamine (2 g), quinine (0.2 g), 2-n-pentyl-3-hydroxy-4-cyclopentenone (16.8 g) and toluene (30 g) were charged, and the mixture was stirred under a nitrogen stream at a temperature of 40° to 70° C. for 5 hours. After completion of the reaction, the mixture was treated and purified in the same manner as in Example 50 to obtain 2-n-pentyl-4-phenylthio-2-cyclopentenone (24.7 g). Yield, 95%. $n_D^{20}$ 1.5706.

EXAMPLE 53

Into the same flask as used in Example 1, triethylamine (5 g), 2-n-pentyl-3-hydroxy-3-methyl-4-cyclopentenone (18.2 g) and toluene (30 g) were charged, and hydrogen sulfide (8 g) was introduced into the mixture at a temperature of 15° to 30° C. Thereafter, the reaction mixture was stirred at a temperature of 50° to 70° C. for 4 hours. After completion of the reaction, the mixture was washed with an acid and water in order. The organic layer was separated and concentrated to obtain 2-n-pentyl-3-methyl-4-mercapto-2-cyclopentenone (18.0 g). Yield, 91%. $n_D^{20}$ 1.5212.

EXAMPLE 54

Into the same flask as used in Example 1, triethylamine (10 g), mercaptoacetic acid (30 g) and toluene (50 g) were charged, and 2-allyl-3-hydroxy-3-methyl-4-cyclopentenone (15.2 g) was dropwise added thereto at a temperature of 20° to 40° for 1 hour. Thereafter, the reaction mixture was stirred at a temperature of 50° to 70° C. for 4 hours. After completion of the reaction, the mixture was evaporated under reduced pressure. The residue was dissolved in a 5% aqueous solution of sodium bicarbonate (100 g), and undissolved materials were filtered off. The filtrate was treated with an acid and extracted with diethyl ether. Diethyl ether was evaporated off from the organic layer to obtain 2-allyl-3-methyl-4-carboxymethylthio-2-cyclopentenone (20.5 g). Yield, 90.5%. $n_D^{20}$ 1.5567.

EXAMPLE 55

Into the same flask as used in Example 1, 2-(2'-cis-pentenyl)-3-hydroxy-3-methyl-4-cyclopentenone (18.0 g), pyridine (6 g), cyclohexylmercaptan (36 g) and toluene (20 g) were charged and stirred at a temperature of 40° to 80° for 6 hours. After completion of the reaction, the mixture was treated and purified in the same manner as in Example 50 to obtain 2-(2'-cis-pentenyl)-3-methyl-4-cyclohexylthio-2-cyclopentenone (25.3 g). Yield, 91%. $n_D^{20}$ 1.5203.

EXAMPLE 56

Into the same flask as used in Example 1, 2-hydroxyethylmercaptan (35 g) and tetrahydrofuran (10 g) were charged, and sodium hydride (0.6 g) was added thereto at a temperature of 10° to 20° C. At the same temperature, the reaction mixture was stirred for 1 hour. Thereafter, 2-allyl-3-hydroxy-3-methyl-4-cyclopentenone (15.2 g) was dropwise added thereto at a temperature of 15° to 30° C. for 1 hour, followed by stirring at the same temperature for 2 hours and at a temperature of 40° to 70° C. for 3 hours. After completion of the reaction, the mixture was treated in the same manner as in Example 1 to obtain 2-allyl-3-methyl-4-(2'-hydroxyethylthio)-2-cyclopentenone (20.4 g). Yield, 96 %. $n_D^{20}$ 1.5243.

EXAMPLES 57 to 67

In the same manner as above, there were prepared the cyclopentenone derivatives (I) as shown in Table 3, wherein the amount of the 3-hydoxy-4-cyclopentenone compound (II) used was one part.

TABLE 3

| Example No. | Starting materials 3-Hydroxy-4-cyclopentenone compound (II) $R^1$ | $R^2$ | Nucleophilic agent (III) (part) | Catalyst (part) | Solvent (part) | Reaction condition Temperature (°C.) | Time (hr) | Cyclopentenone derivative (I)*[1] —$SR^6$ | Physical property | Yield (%) |
|---|---|---|---|---|---|---|---|---|---|---|
| 60 | —CH$_3$ | —CH$_2$CH=CH$_2$ | Thioacetic acid (2) | Triethylamine (1/5) | Tetrahydrofuran (1) | 20–60 | 4 | —S—COCH$_3$ | $n_D^{20}$ 1.5423 | 94 |
| 61 | —CH$_3$ | —CH$_2$CH=CH$_2$ | Benzylmercaptan (2) | Sodium hydride (1/10) | Tetrahydrofuran (1) | 15–40 | 3 | —S—CH$_2$— | $n_D^{20}$ 1.5765 | 92 |
| 62 | —CH$_3$ | —CH$_2$CH=CH$_2$ | Thiophenol (2.5) | Triethylamine (1/5) | Toluene (2) | 30–70 | 5 | —S— | M.P. 65° C. | 96 |

TABLE 3-continued

| Example No. | Starting materials 3-Hydroxy-4-cyclo-pentenone compound (II) R¹ | R² | Nucleophilic agent (III) (part) | Catalyst (part) | Solvent (part) | Reaction condition Temperature (°C.) | Time (hr) | Cyclopentenone derivative (I)*¹ —SR⁶ | Physical property | Yield (%) |
|---|---|---|---|---|---|---|---|---|---|---|
| 63 | —CH₃ | —CH₂CH=CH₂ | Hydrogen sulfide (0.5) | Triethylamine (1/4) | Toluene (2) | 30–70 | 4 | —S—H | $n_D^{20}$ 1.5486 | 90 |
| 64 | —CH₃ |  | n-Butylmercaptan (1.5) | Triethylamine (1/10) | Toluene (2) | 50–80 | 4 | —S—C₄H₉(n) | $n_D^{20}$ 1.5188 | 95 |
| 65 | —H | 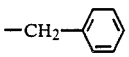 | 2-Propenyl-mercaptan (2) | Triethylamine (1/5) | Toluene (1) | 50–70 | 4 | —S—CH₂CH=CH₂ | $n_D^{20}$ 1.5780 | 90 |
| 66 | —CH₃ | —C₅H₁₁(n) | p-Chlorothiophenol (1) | Triethylamine (1/3) | Toluene (2) | 40–70 | 5 | 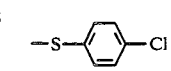 | $n_D^{20}$ 1.5692 | 94 |
| 67 | —CH₃ | —CH₂C≡CH | Thiophenol (2) | Pyridine (1/3) | Tetrahydrofuran (1) | 35–75 | 4 | 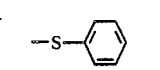 | $n_D^{20}$ 1.5809 | 85 |
| 68 | —CH₃ | —CH₂CH=CH₂ | 2-Mercapto-thiophene (2) | Triethylamine (1/4) | Dimethylformamide (1) | 40–80 | 4 |  | $n_D^{20}$ 1.5683 | 94 |
| 69 | —CH₃ | —CH₂CH=CH₂ | p-Chlorothiophenol (2) | Pyridine (1/4) | Toluene (2) | 50–70 | 4 |  | $n_D^{20}$ 1.5845 | 93 |
| 70 | —CH₃ | —CH₂CH=CH₂ | 2,4-Dichloro-thiophenol (2) | Triethylamine (1/4) | Toluene (2) | 50–70 | 5 |  | $n_D^{20}$ 1.5872 | 95 |

Note:
R¹ and R² in the cyclpentenone derivatives (I) have the same meanings as in the 3-hydroxy-4-cyclopentenone compound (II).

What is claimed is:

1. A process for preparing cyclopentenone derivatives of the formula:

(I)

wherein

R¹ is hydrogen, lower alkyl or lower alkenyl;
R² is hydrogen, lower alkyl, lower alkenyl, lower alkynyl, cycloalkyl, phenyl, phenyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, naphthyl, naphthyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl(lower alkyl), phenyl(lower alkyl) substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl; naphthyl(lower alkyl), and naphthyl(lower alkyl) substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl; and

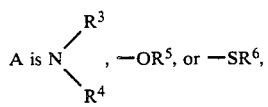, —OR⁵, or —SR⁶, wherein,

R³ is hydrogen, lower alkyl, lower alkyl substituted with at least one member selected from the group consisting of halogen, lower alkyl, lower alkenyl, lower alkoxy, lower alkoxycarbonyl, lower alkanoyloxy, hydroxyl, hydroxy (lower)alkyl, phenyl, thienyl, furyl and pyridyl, lower alkenyl; lower alkenyl substituted with at least one member from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, cycloalkyl, cycloalkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl, phenyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, naphthyl, naphthyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl(lower)alkyl, phenyl(lower)alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, naphthyl(lower)alkyl, naphthyl lower alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, lower alkoxy, hydroxyl, a heterocyclic ring containing oxygen, nitrogen or sulfur, and a heterocyclic ring containing oxygen, nitrogen or sulfur substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl;

$R^4$ is hydrogen, lower alkyl, lower alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, lower alkenyl, lower alkenyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl, phenyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl; naphthyl, naphthyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl(lower)alkyl, phenyl(lower)alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, naphthyl(lower)alkyl, or naphthyl(lower)alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, or $R^3$ and $R^4$ when taken together with the adjacent nitrogen atom represent a heterocyclic group containing oxygen, nitrogen, or sulfur, or a heterocyclic group consisting oxygen, nitrogen, or sulfur substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl;

$R^5$ is lower alkyl, lower alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, lower alkenyl, lower alkenyl substituted with at least one member selected from the group consisting of halogen, lower alkyl, lower alkenyl, lower alkoxy, lower alkoxycarbonyl, lower alkanoyloxy, hydroxyl, hydroxy (lower)alkyl, phenyl, thienyl, furyl and pyridyl, lower alkadienyl, lower alkadienyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, cycloalkyl, cycloalkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl, phenyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, naphthyl, naphthyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl(lower)alkyl, phenyl(lower)alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, naphthyl(lower)alkyl, naphthyl(lower)alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, a heterocyclic group containing oxygen, nitrogen, or sulfur, or a heterocyclic group containing oxygen, nitrogen or sulfur substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl;

$R^6$ is hydrogen, lower alkyl, lower alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, lower alkenyl, lower alkenyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, cycloalkyl, cycloalkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl, phenyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, naphpthyl, napthyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenyl(lower)alkyl, phenyl(lower)alkyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, naphthyl(lower)alkyl, naphthyl(lower)alkyl substituted with at least one member selected from the group consisting of halogen, lower alkyl, lower alkenyl, lower alkoxy, lower alkoxycarbonyl, lower alkanoyloxy, hydroxyl, hydroxy(lower)-alkyl, phenyl, thienzyl, furyl and pyridyl, lower alkanoyl, benzoyl, benzoyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, phenylalkanoyl, phenylalkanoyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, alkoxycarbonyl, alkoxycarbonyl substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl, a heterocyclic group containing oxygen, nitrogen or sulfur, or a heterocyclic group containing oxygen, nitrogen, or sulfur substituted with at least one member selected from the group consisting of halogen, lower alkyl, lower alkenyl, lower alkoxy, lower alkoxycarbonyl, lower alkanoyloxy, hydroxyl, hydroxy(lower)alkyl, phenyl, thienyl, furyl and pyridyl;

which comprises reacting a 3-hydroxy-4-cyclopentenone compound of the formula:

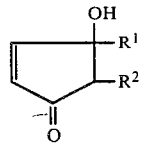 (II)

wherein $R^1$ and $R^2$ are each as defined above with a nucleophilic agent of the formula:

 (III)

wherein A is as defined above, in the presence or absence of an acidic or basic catalyst at a temperature or $-10°$ to $120°$ C.

2. The process according to claim 1, which is carried out in the presence of an acidic catalyst.

3. The process according to claim 1, which is carried out in the presence of a basic catalyst.

4. The process according to claim 1, wherein the heterocyclic group containing oxygen, nitrogen or sulfur is a member selected from the group consisting of pyrrolidino, piperidino, morpholino, thiomorpholino, pyridyl, thienyl, and furyl.

5. The process according to claim 2, wherein the acidic catalyst is hydrochoric acid, sulfuric acid, phosphoric acid, acetic acid, methanesulfonic acid, benzenesulfonic acid or toluenesulfonic acid.

6. The process according to claim 3, wherein the basic catalyst is an alkali metal or a salt thereof, oxide, alkoxide, hydride or amide or a tertiary amine or a quarternary ammoniom salt thereof.

7. The process according to claim 1, wherein the reaction is carried out in an inert solvent.

8. The process according to claim 7, wherein the inert solvent is tetrahydrofuran, dioxane, acetone, dimethylformamide, benzene, toluene, chloroform or diethyl ether.

9. The process according to claim 1, wherein the reaction is carried out under an anhydrous condition.

* * * * *